United States Patent
Lin

(10) Patent No.: US 10,272,245 B2
(45) Date of Patent: Apr. 30, 2019

(54) NEURAL SENSING METHOD FOR RETINA APPLICATION AND DEVICE THEREOF

(71) Applicant: Po-Kang Lin, Taipei (TW)

(72) Inventor: Po-Kang Lin, Taipei (TW)

( * ) Notice: Subject to any disclaimer, the term of this patent is extended or adjusted under 35 U.S.C. 154(b) by 0 days.

(21) Appl. No.: 15/874,898

(22) Filed: Jan. 19, 2018

(65) Prior Publication Data

US 2018/0140840 A1    May 24, 2018

Related U.S. Application Data

(63) Continuation-in-part of application No. 15/345,538, filed on Nov. 8, 2016, now abandoned.

(51) Int. Cl.
*A61N 1/05*     (2006.01)
*A61N 1/36*     (2006.01)

(52) U.S. Cl.
CPC ........ *A61N 1/36046* (2013.01); *A61N 1/0543* (2013.01)

(58) Field of Classification Search
CPC .......................... A61N 1/36046; A61N 1/0543
See application file for complete search history.

(56) References Cited

U.S. PATENT DOCUMENTS

2015/0374990 A1*  12/2015  Fan ............... A61N 1/36046
                                                          607/54

* cited by examiner

*Primary Examiner* — Paula J Stice
(74) *Attorney, Agent, or Firm* — Lin & Associates Intellectual Property, Inc.

(57) ABSTRACT

A neural sensing method includes the steps of: configuring an array of sensing units on a retina of a user, each of the sensing units detecting a signal and generating a sensed signal; generating a control signal by a control signal generator and transmitting the control signal to at least one electrode installed in a periphery of each of the sensing units; isolating each of the sensed signals by the control signal, thereby suppressing the mutual interference between the sensed signals by the control signal; and generating and outputting a processed signal to at least one neuron via a signal processing module with reference to the control signal and the sensed signals. The control signal has a signal strength lower than the sensing threshold of the at least one neuron.

16 Claims, 8 Drawing Sheets

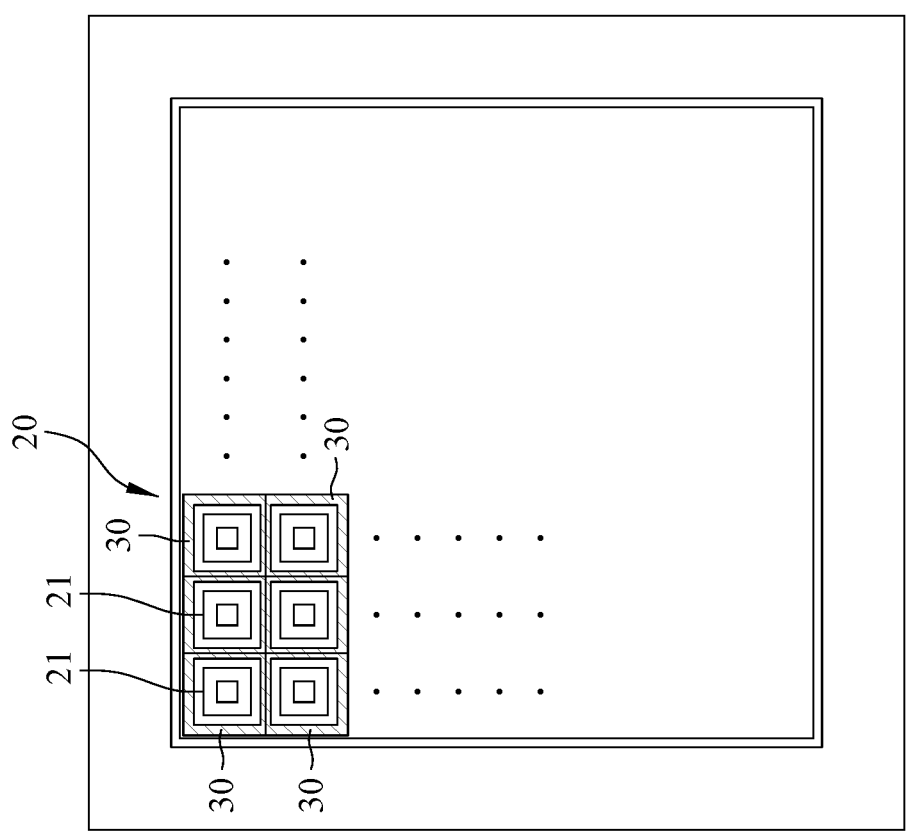

NEURAL SENSING METHOD FOR RETINA APPLICATION AND DEVICE THEREOF

CROSS-REFERENCE TO RELATED APPLICATIONS

This application is a continuation-in-part application of U.S. application Ser. No. 15/345,538, the disclosure of which is hereby incorporated by reference herein.

BACKGROUND OF THE INVENTION

1. Field of the Invention

The present invention relates to a neural sensing method and device, and more particularly, relates to a neural sensing method and device thereof capable of avoiding interferences between sensed signals for stimulating the neurons caused by the high signal amplitude of received signals.

2. The Prior Arts

In 2002, the Second Sight Medical Products Inc. performed human transplant operations on six blind patients utilizing its own product: the experimental electronic eye Argus I. Argus I is a bionic eye with a resolution of 16 pixels. With the differences in the brightness generated by the light reflection from the surfaces of the objects, Argus I gave blind patients the ability to distinguish the outlines of objects. In 2006, the company announced a second-generation product Argus II, which boosts the resolution up to 60 pixels. Argus II provides a better resolution and higher accuracy regarding the image recognition for the users.

The device of the experimental electronic eye Argus II includes an image capturing device disposed outside of the body of a user and an image receiving chip placed inside the body of the user. The image capturing device includes a frame, a miniature camera, an image processing unit and a wireless communication module. The frame is removable worn on the face of the user, and the miniature camera and the wireless communication module are equipped on the frame. The miniature camera is able to capture images in front of the user to generate imaging information. In addition to being disposed on the frame, the image processing unit is also connected to the miniature camera. The image processing unit is able to receive the imaging information generated by the miniature camera and further generates digital image information. At this time, the wireless communication module receives the digital image information generated by the image processing unit and transmits the digital image information to the image receiving chip. The image receiving chip is disposed on a retina of the user and is connected to at least one ganglion cell on the retina of the user. The image receiving chip is able to convert the digital image information into a neural spike, and is able to transmit the neural spike to the brain of the user via the at least one ganglion cell, thereby allowing the user to recognize an image.

In order to enhance the resolution of image and the recognition results perceived by the user, it is inevitable for the conventional image receiving chip to increase the number of photosensitive units within a limited area of the chip so as to increase the pixel value. By doing so, it would shorten the distance between each photosensitive unit, and the sensed signals (herein, the sensed signals generated by the photosensitive units each has a sensed signal strength) of the photosensitive units are likely to interfere with each other during the operation. As a result, such configuration may have a pixel value that is even lower than the original effective pixel value. As shown in FIG. 1, when the sensed signals of two adjacent photosensitive units 10 are interfering with each other, and when the stacked signal between the two adjacent photosensitive units 10 is higher than a threshold of at least one ganglion cell of the user, the two adjacent photosensitive units 10 will be recognized as one photosensitive unit 11 with a larger area by the at least one ganglion cell of the user, and the received sensed signals will be transmitted to the brain of the user. If the sensed signals of all the photosensitive units are interfering with each other, the user will only be able to perceive a vague shape of light and shadow, thus losing the ability to identify images by the outline of the object. As a result, such image receiving chip with a high number of pixels may lose its ability to enhance the resolution of image and recognition results for the users.

Therefore, there is an urgent need for the industry to develop a neural sensing device that may prevent the sensed signals for stimulating neurons from interfering with each other because of the high signal amplitude of the received signals. It is preferred for such neural sensing device to have the characteristics of a small body, high neural sensing sensitivity and high accuracy.

SUMMARY OF THE INVENTION

Based on the above reasons, a primary objective of the present invention is to provide a neural sensing device. Such neural sensing device is able to prevent the sensed signals for neurons from interfering with each other due to the high signal amplitude of the received signals while maintaining a high neural sensing sensitivity and high accuracy.

For achieving the foregoing objectives, the present invention provides a neural sensing method for retina application. The method includes the steps of: providing an array of sensing units, wherein each of the sensing units of the array of sensing units detects a signal and generates a sensed signal; generating and transmitting a control signal to at least one electrode installed in the periphery of each of the sensing units of the array of sensing units by a control signal generator, wherein the control signal generator is connected to the at least one electrode; suppressing the mutual interference between the sensed signals of the sensing units by the control signal; outputting the sensed signals by the array of sensing units to the signal processing module; and generating a processed signal by the signal processing module for stimulating at least one neuron; wherein the at least one neuron has a sensing threshold, the sensed signal above the sensing threshold is perceived by the at least one neuron, and the signal strength of the control signal is lower than the sensing threshold. It is widely known in the art that a neuron has a sensing threshold and a neuron can only perceive a received signal that has a signal strength greater than the sensing threshold.

Preferably, the control signal is generated before the sensed signals, or the control signal and the sensed signal are generated at the same time.

Preferably, the array of the sensing units is an array of photodiodes of an electronic retina chip, and each of the sensing units is a photodiode for replacing a photoreceptor cell on a human retina.

Preferably, the control signal generator is disposed at one side of the array of the sensing units of an electronic retina chip, and the control signal generator transmits the control signal to the signal processing module.

Preferably, the control signal generator is connected to electrodes that are installed and connected to left side and right side of each of the sensing units of the array of sensing units, and the control signal generator transmits the control signal to the left side and the right side of each of the sensing unit via the electrodes.

Preferably, the control signal generator is connected to a ring electrode that is installed and connected to the periphery of each of the sensing units of the array of sensing units, and the control signal generator transmits the control signal to the periphery of each of the sensing unit via the ring electrode.

Preferably, the processed signal outputted by the signal processing module is used for stimulating at least one ganglion cell of a human retina.

Preferably, the processed signal is at least one electrical pulse.

In addition, the present invention also provides a neural sensing device for retina application. The neural sensing device includes: an array of sensing units, including a plurality of sensing units, wherein each of the sensing units of the array of sensing units detects a signal and generates a sensed signal; a control signal generator, connected to the array of sensing units, generating and transmitting a control signal to at least one electrode installed in the periphery of each of the sensing units of the array of sensing units, wherein the control signal generator is connected to the at least one electrode, and the mutual interference between the sensed signals of the sensing units is suppressed by the control signal; and a signal processing module, connected to the array of sensing units and the control signal generator, wherein the signal processing module generates a processed signal for stimulating at least one neuron; wherein the at least one neuron has a sensing threshold, the sensed signal above the sensing threshold is perceived by the at least one neuron, and the signal strength of the control signal is lower than the sensing threshold.

Preferably, the control signal is generated before the sensed signal, or, the control signal and the sensed signal are generated at the same time.

Preferably, the array of sensing units is an array of photodiodes of an electronic retina chip, and each of the sensing units is a photodiode for replacing a photoreceptor cell on a human retina.

Preferably, the control signal generator is disposed at one side of the array of the sensing units of an electronic retina chip, and the control signal generator transmits the control signal to the signal processing module.

Preferably, the control signal generator is connected to electrodes that are installed and connected to left side and right side of each of the sensing units of the array of sensing units, and the control signal generator transmits the control signal to the left side and the right side of each of the sensing unit via the electrodes.

Preferably, the control signal generator is connected to a ring electrode that is installed and connected to the periphery of each of the sensing units of the array of sensing units, and the control signal generator transmits the control signal to the periphery of each of the sensing units via the ring electrode.

Preferably, the processed signal outputted by the signal processing module of the neural sensing device is used for stimulating at least one ganglion cell of a human retina.

Preferably, the processed signal can be at least one electrical pulse.

When using the neural sensing device of the present invention, the control signal generator generates and transmits the control signal to the periphery of each of the sensing units, so the control signal suppresses the mutual interferences between the sensed signals of the sensing units. As a result, mutual interferences can be suppressed, and the at least one neuron can be prevented from malfunction. When the array of sensing units senses image and/or light sources, each of the sensing units on the array of sensing units generates the sensed signal according to the strength distribution of the light of the image and/or light source. Since the control signals suppress the mutual interference as described above, when the array of sensing units senses the variation in the intensive distribution of the image and/or light source, the at least one neuron can be prevented from being interfered by multiple sensed signals. In this way, the present invention is able to provide a device with high neural sensing sensitivity and high accuracy.

BRIEF DESCRIPTION OF THE DRAWINGS

FIG. 3c is a schematic diagram showing the appearance of an array of sensing units of the neural sensing device according to the third embodiment of the present invention.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention. The present invention may also be implemented or applied as other embodiments that are not described herein, and each detail described in the specification may also be changed or modified according to different aspects without departing from the spirit of the present invention.

It should be noted that the structure, ratio and size shown in the accompanying drawings of the present invention are only for illustrative purposes of the disclosure described in the specification, so those who are skilled in the art may have a better understanding of the present invention. The structure, ratio and size shown in the accompanying drawings are not to limit the scope of the present invention; therefore, they do not represent any substantive technical meanings. Any structures modifications, ratios changes or size adjustment made to the drawings should still be considered to be within the scope of the present invention as long as they do not affect the effects and purposes thereof.

Hereafter, a neural sensing device will be described in accordance with a first embodiment of the present invention.

Figure 2:
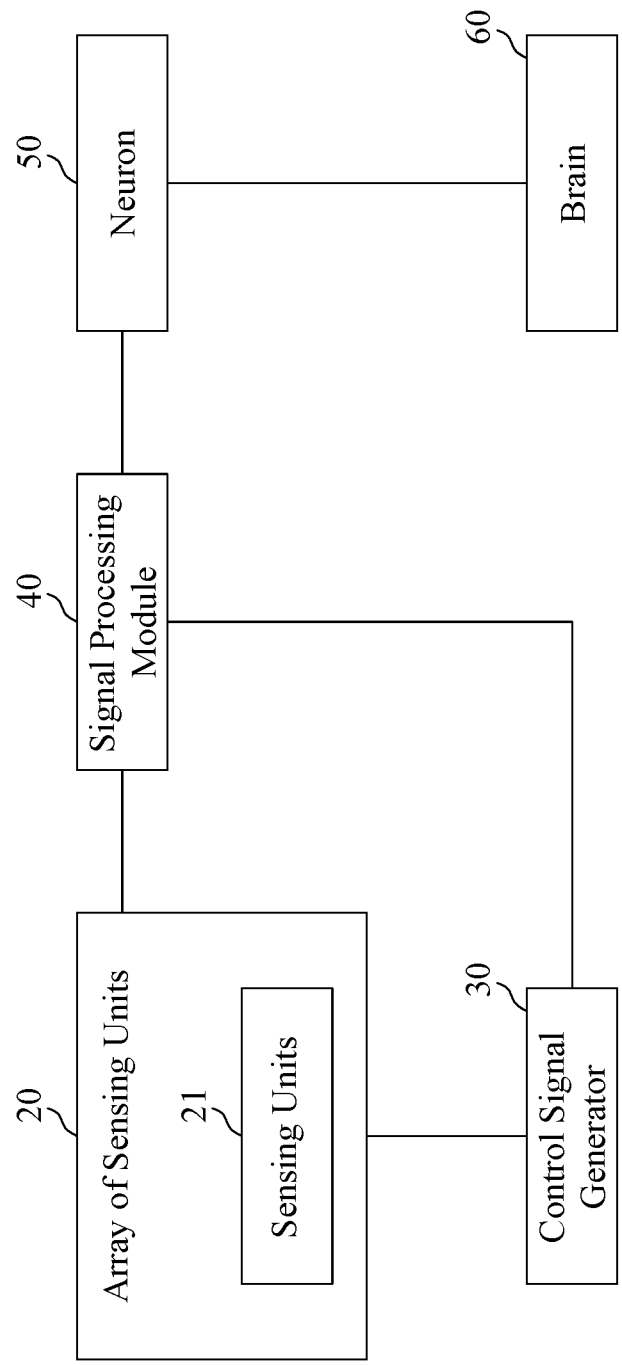
FIG. 2 is a block diagram schematically showing the circuits of a neural sensing device according to a first embodiment of the present invention.
Figure 3A:
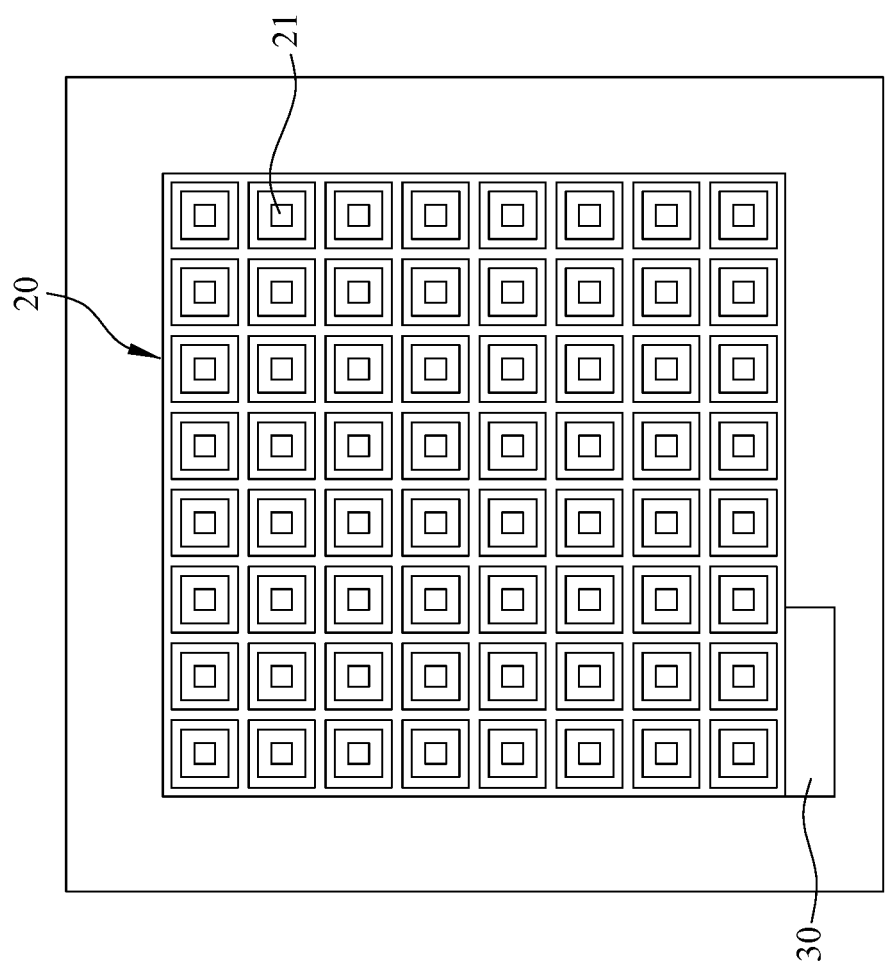
FIG. 3a is a schematic diagram showing the appearance of an array of sensing units of the neural sensing device according to the first embodiment of the present invention.
Figure 4:
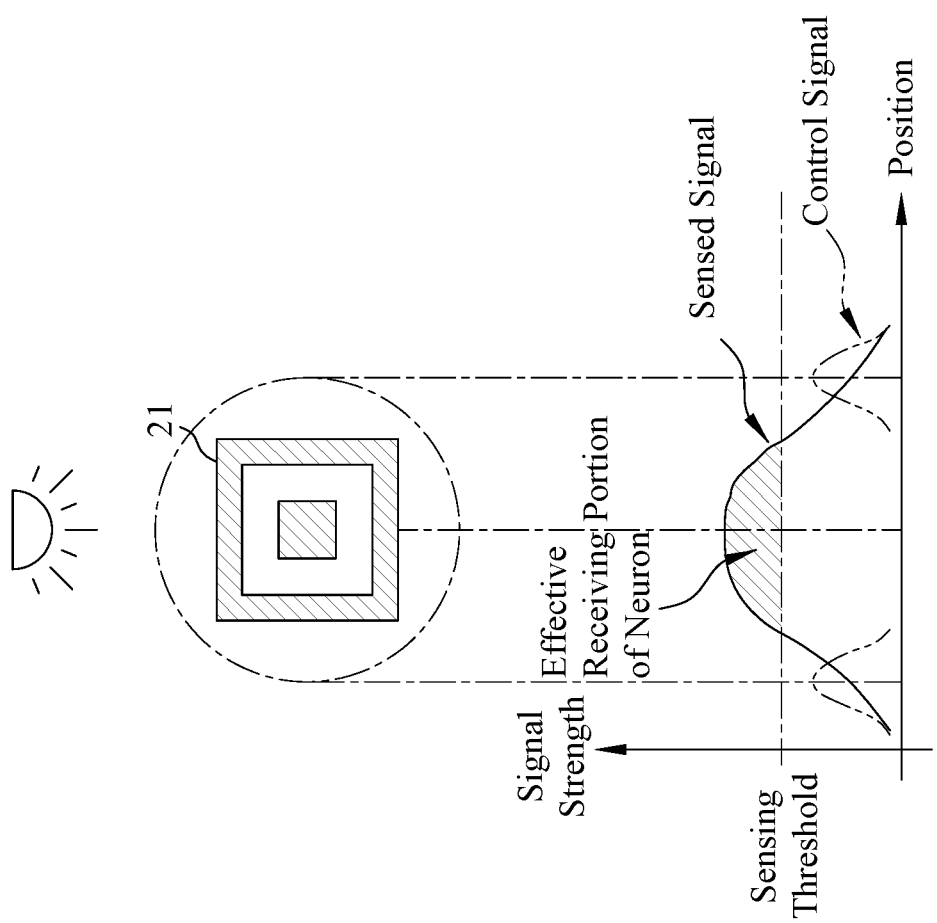
FIG. 4 is a schematic diagram illustrating the coupling between a sensed signal and a control signal of the neural sensing device according to the first embodiment of the present invention.

As shown in FIG. 2 and FIG. 3a, the neural sensing device of the present invention includes: an array of sensing units 20, a control signal generator 30 and a signal processing module 40. The array of sensing units 20 may include a plurality of sensing units 21. Each of the plurality of sensing units 21 detects a signal and generates a sensed signal, and the signal strength of each of the sensed signals is higher than a sensing threshold of at least one neuron 50. In such a way, the at least one neuron 50 may sense effective information and transmit such information to the brain 60. According to the first embodiment of the present invention, the array of sensing units 20 is an array of photodiodes of an electronic retina chip. Each of the sensing units 21 is a photodiode that can be used to replace a photoreceptor cell on a human retina; namely, each of the sensing units 21 is treated as a pixel of an image to be sensed. Each sensing unit 21 is able to convert the photon energy emitted thereto into electronic ionization energy, and further output it as electric energy. In such a way, sensed signals corresponding to the photon energy can be generated, and the sensed signals can be transmitted to the signal processing module 40. It is important to note that when a control signal is transmitted to a surrounding of each sensing unit 21, the control signal suppresses the electronic ionization energy of the sensing unit 21 as shown in FIG. 4, or it can be regarded that the right side and the left side of the sensed signal will be blocked by the control signal. As a result, interference between the sensed signals of adjacent sensing units can be prevented. In addition, in other embodiments of the present invention, the control signal generator 30 may be integrated into the structure of the electronic circuits (not shown) of each of the sensing units 21; as a result, the overall structure of the device may further be simplified.

Figure 3B:
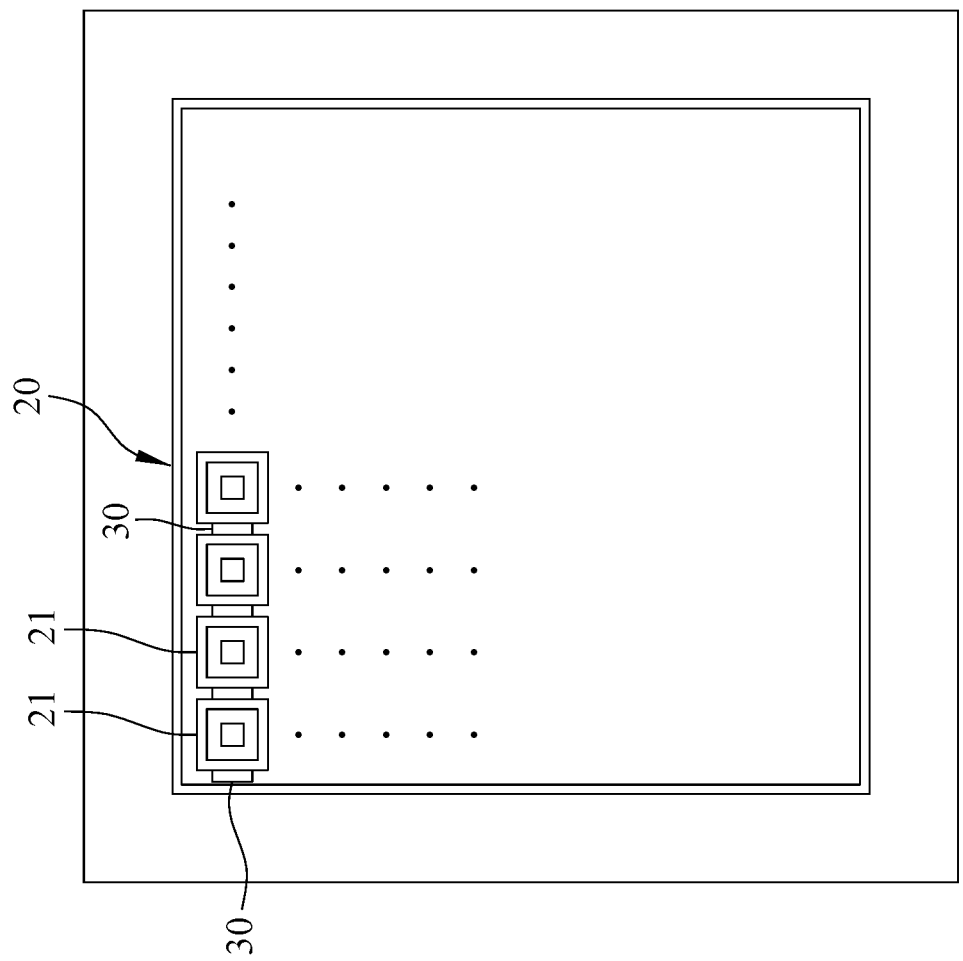
FIG. 3b is a schematic diagram showing the appearance of an array of sensing units of the neural sensing device according to the second embodiment of the present invention.

As shown in FIG. 2 to FIG. 4, the control signal generator 30 may be connected to the array of sensing units 20, and the control signal generator 30 is an active element and generates a control signal to the periphery of each sensing unit 21 in the array of sensing units, there is no feedback system in the neural sensing device of the present invention. In the second embodiment, as shown in FIG. 3b, the control signal generator 30 can be connected to electrodes that are installed and connected to the right and left sides of each sensing unit 21, and generate a control signal to the right and left side of each sensing unit 21 in the array of sensing units, as shown in FIG. 4. In the third embodiment, as shown in FIG. 3c, the control signal generator 30 can be connected to a ring electrode that is installed and connected to the periphery of each sensing unit 21, and generate a control signal to the periphery of each sensing unit 21 in the array of sensing units, as shown in FIG. 4.

Figure 1:
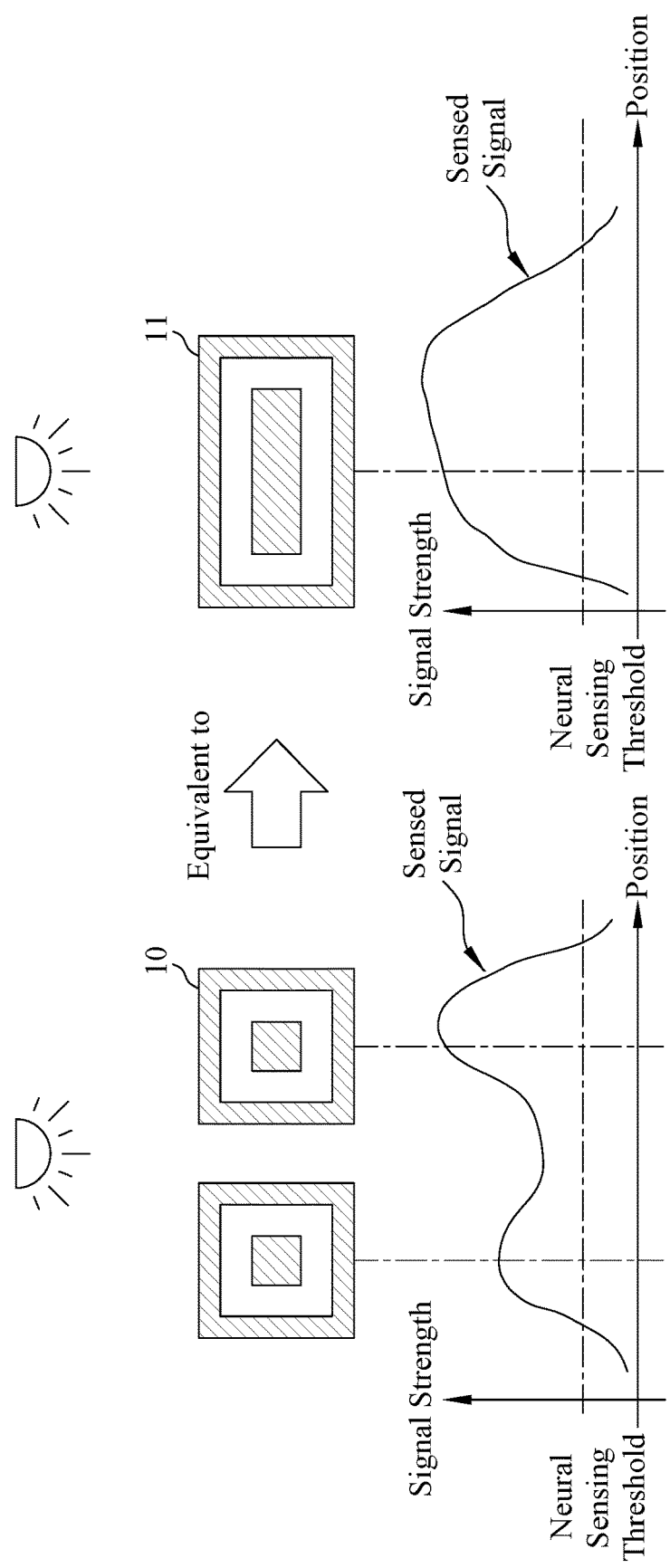
FIG. 1 is a schematic diagram illustrating the interference between the sensed signals of two adjacent photosensitive units of the experimental electronic eye of the prior arts.

The signal strength of the control signal is lower than the sensing threshold as shown in FIG. 4, so the control signal suppresses the mutual interference between the sensed signals of the sensing units. Also, the signal strength of the control signal is lower than the sensing threshold of the at least one neuron and therefore is not perceived by the neuron. Because the sensed signal is suppressed in the surrounding of each sensing unit as shown in FIG. 4, the interference caused by the overlapping of two adjacent sensed signals shown in FIG. 1 no longer exists. As a result, the control signal effectively isolates the sensed signal of each sensing unit. Herein, the control signal may be generated before the sensed signal, or the control signal may be generated simultaneously with the sensed signal. In such a way, each of the sensed signals may be isolated by the control signal, thereby suppressing interference. Further, once the sensed signals are isolated from each other by the control signal, the sensed signals are considered as isolated signals and are prevented from interfering with each other; therefore, the signal strength of each sensed signal may be further enhanced. It should be understood that each of the sensed signals has a sensed signal strength that must be greater than the sensing threshold of the neuron so as to be perceived by the neuron. In one embodiment of the present invention, the control signal strength is adjusted to be lower than the sensing threshold. Thereafter, each of the sensed signals may be isolated with each other via the control signal, thereby suppressing interference between the sensed signals. The control signal strength of each control signal is lower than the sensing threshold of the at least one neuron 50 so as to prevent the at least one neuron 50 from sensing any effective information of the control signal. According to the theory of neuron transmission, after the at least one neuron is action potential simulated, because of the inactivation of the sodium ion (N) channel and a refractory period, the at least one neuron 50 cannot respond to other action potentials simulated when it is under the refractory period. The first embodiment of the present invention takes advantage of such a characteristic to put the at least one neuron 50 in the periphery of each sensing unit 21 into the refractory period temporarily, and refrain the sensed signal generated by each sensing unit 21 from creating chain reactions at the peripheries thereof, thereby preventing the interferences between the sensed signals of the sensing units. As a result, the situation in which the stacked signal strength between the adjacent sensing units 21 is higher than the sensing threshold of the at least one neuron 50 is prevented from happening. Furthermore, since the signal strength of each control signal never reaches the sensing threshold of the at least one neuron 50, effective information of the control signal will never be constructed for the at least one neuron 50, thus the recognition results of the brain 60 toward the image to be sensed may stay unaffected. According to the first embodiment of the present invention, the control signal generator 30 may be configured at a side of the array of sensing units 20 of an electronic retina chip, and the control signal generator 30 may transmit the control signal to the signal processing module 40.

Moreover, in other embodiment of this application, the signal strength of the control signal generated by the control signal generator 30 is negative, thereby offset the right and left side of the sensed signals.

Figure 5:
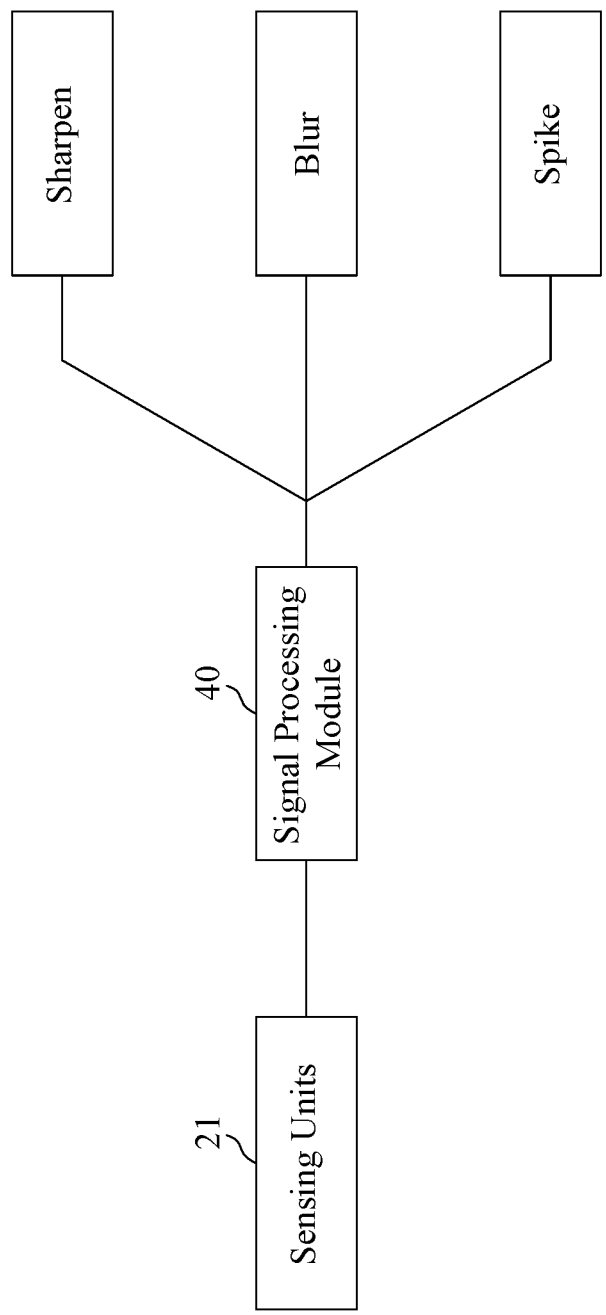
FIG. 5 is a schematic diagram illustrating the signal processing of the neural sensing device according to the first embodiment of the present invention.
Figure 6:
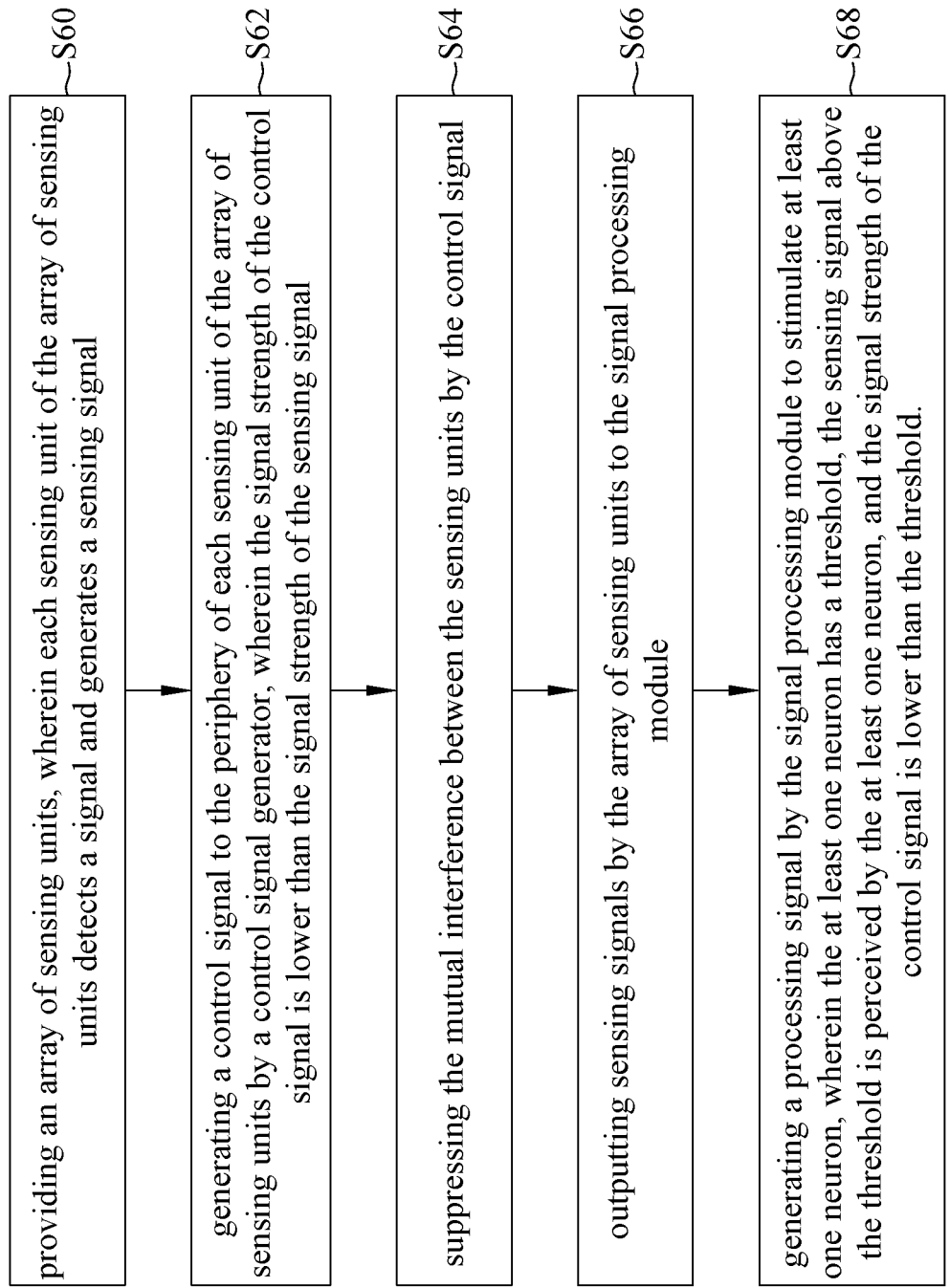
FIG. 6 is a flow chart illustrating a neural sensing method for retinal application according to a first embodiment of the present invention.

As shown in FIG. 2 and FIG. 5, the signal processing module 40 may be connected to the array of sensing units 20 and the control signal generator 30, and may be configured to generate and output a processed signal to the at least one neuron 50. According to the first embodiment of the present invention, neural sensing device may be directly connected to at least one ganglion cell on a human retina, so the signal processing module 40 may be used to replace the bipolar cell and/or horizontal cell on the human retina. Each of the at least one ganglion cells is a gangliform body structure formed by the congregation of the at least one neuron 50 of the same function. The bipolar cells are capable of enhancing the difference between the signal edges to increase the image sharpness perceived by the brain 60; that is, sharpening the image perceived by the brain 60. On the other hand, the horizontal cells are capable of reducing the difference in the signal edges to decrease the image sharpness perceived by the brain 60; that is, blurring the image perceived by the brain 60.

In the first embodiment of the present invention, the processed signal may be at least one spike. After the signal processing module 40 couples the sensed signals of each sensing unit 21 with the control signals, the signal process module 40 then generates and outputs the at least one spike to the at least one neuron 50.

When using the neural sensing device of the present invention, first, the array of sensing units 20 is installed on the retina of a user, and the at least one sensing unit 21 of the array of sensing units 20 is configured to be facing outward of the user to sense images outside of the retina of the user. The signal processing module 40 is then connected to the at least one ganglion cell on the human retina to transmit the processed signal to the at least one neuron 50. Subsequently, the control signal generator 30 generates the control signal to the periphery of each sensing unit 21, so the control signal is isolated between the sensed signals between each sensing units; in such a way, interferences between the sensed signals can be suppressed, and the at least one neuron 50 can be prevented from malfunction. Herein, the control signal may be generated before the sensed signal, or the control signal may be generated simultaneously with the sensed signal. In such a way, each of the sensed signals may be isolated by the control signal, thereby suppressing interference. When the array of sensing units 20 senses image and/or light sources, each sensing unit 21 on the array of sensing units 20 generates the sensed signal according to the strength distribution of the light of the image and/or light source. Since the control signals are isolated between each sensed signals as described above, when the array of sensing units 20 senses variation in the intensive distribution of the light of the image and/or light source, the at least one neuron 50 can be prevented from being interfered by multiple sensed signals at the same time. In this way, the present invention is able to provide a device with high neural sensing sensitivity and high accuracy.

On the other hand, referring to FIGS. 2-6, the present invention also provides a neural sensing method for retina application. The neural sensing method of the present invention includes Steps S60-S68, which are further described in the following section. Step S60: providing an array of sensing units, wherein each of the sensing units of the array of sensing units detects a signal and generates a sensed signal. Step 62: generating and transmitting a control signal to at least one electrode installed in the periphery of each of the sensing units of the array of sensing units by a control signal generator, wherein the control signal generator is connected to the at least one electrode. Step S64: suppressing the mutual interference between the sensed signals of the sensing units by the control signal. Step S66: outputting the sensed signals by the array of sensing units to the signal processing module. Step S68: generating a processed signal by the signal processing module for stimulating at least one neuron. Herein, the at least one neuron has a sensing threshold, the sensed signal above the sensing threshold is perceived by the at least one neuron, and the signal strength of the control signal is lower than the sensing threshold.

Furthermore, in the neural sensing method provided by the present invention, the control signal may be generated before the sensed signal, or the control signal may be generated simultaneously with the sensed signal. In such a way, each of the sensed signals may be isolated by the control signal, thereby suppressing interference. Moreover, the array of the sensing units is an array of photodiodes of an electronic retina chip, and each of the sensing units is a photodiode for replacing a photoreceptor cell on a human retina.

Besides, in the neural sensing method provided by the present invention, the control signal generator can be connected to electrodes that are installed and connected to the right and left sides of each sensing unit, and generate a control signal to the right and left side of each sensing unit of the array of sensing units via the electrodes. Moreover, the control signal generator can be connected to a ring electrode that is installed and connected to the periphery of each sensing unit, and generate a control signal to the periphery of each sensing unit of the array of sensing units.

According to the neural sensing device for retinal application provided by the present invention, similarly, in the neural sensing method for retinal application, the control signal generator is disposed at a side of the array of the sensing units of an electronic retina chip, and the control signal generator transmits the control signal to the signal processing module. In addition, the neural sensing device can be directly connected to at least one ganglion cell on a human retina.

Although the present invention has been described with reference to the preferred embodiments thereof, it is apparent to those skilled in the art that a variety of modifications and changes may be made without departing from the scope of the present invention which is intended to be defined by the appended claims. In addition, the number of elements disclosed in the specification is only for illustrative purpose but to limit the scope of the present invention. The scope of the present invention should only be defined by the appended claims.

What is claimed is:

1. A neural sensing method for retina application, comprising the steps of:
    providing an array of sensing units, wherein each of the sensing units of the array of sensing units detects a signal and generates a sensed signal;
    generating and transmitting a control signal to at least one electrode installed in a periphery of each of the sensing units of the array of sensing units by a control signal generator, wherein the control signal generator is connected to the least one electrode;
    suppressing mutual interference between the sensed signals of the sensing units by the control signal;
    outputting the sensed signals by the array of sensing units to a signal processing module; and
    generating a processed signal by the signal processing module for stimulating at least one neuron,
    wherein the at least one neuron has a sensing threshold above which a signal received by the at least one neuron can be perceived by the at least one neuron, and a signal strength of the control signal is lower than the sensing threshold.

2. The neural sensing method according to claim 1, wherein the control signal is generated before the sensed signals, or the control signal and the sensed signal are generated at the same time.

3. The neural sensing method according to claim 1, wherein the array of the sensing units is an array of photodiodes of an electronic retina chip, and each of the sensing units is a photodiode for replacing a photoreceptor cell on a human retina.

4. The neural sensing method according to claim 1, wherein the control signal generator is disposed at one side of the array of the sensing units of an electronic retina chip, and the control signal generator transmits the control signal to the signal processing module.

5. The neural sensing method according to claim 1, wherein the control signal generator is connected to electrodes that are installed and connected to left side and right side of each of the sensing units of the array of sensing units, and the control signal generator transmits the control signal to the left side and the right side of each of the sensing units via the electrodes.

6. The neural sensing method according to claim 1, wherein the control signal generator is connected to a ring electrode that is installed and connected to the periphery of each of the sensing units of the array of sensing units, and the control signal generator transmits the control signal to the periphery of each of the sensing units via the ring electrode.

7. The neural sensing method according to claim 1, wherein the processed signal outputted by the signal processing module is used for stimulating at least one ganglion cell of a human retina.

8. The neural sensing method according to claim 1, wherein the processed signal is at least one electrical pulse.

9. A neural sensing device for retina application, comprising:
an array of sensing units, including a plurality of sensing units, wherein each of sensing units of the array of sensing units detects a signal and generates a sensed signal;
a control signal generator, connected to the array of sensing units, generating and transmitting a control signal to at least one electrode installed in a periphery of each of the sensing units of the array of sensing units, wherein the control signal generator is connected to the least one electrode, and mutual interference between the sensed signals of the sensing units is suppressed by the control signal; and
a signal processing module, connected to the array of sensing units and the control signal generator, wherein the signal processing module generates a processed signal for stimulating at least one neuron,
wherein the at least one neuron has a sensing threshold above which a signal received by the at least one neuron can be perceived by the at least one neuron, and a signal strength of the control signal is lower than the sensing threshold.

10. The neural sensing device according to claim 9, wherein the control signal is generated before the sensed signals, or the control signal and the sensed signal are generated at the same time.

11. The neural sensing device according to claim 9, wherein the array of the sensing units is an array of photodiodes of an electronic retina chip, and each of the sensing units is a photodiode for replacing a photoreceptor cell on a human retina.

12. The neural sensing device according to claim 9, wherein the control signal generator is disposed at one side of the array of the sensing units of an electronic retina chip, and the control signal generator transmits the control signal to the signal processing module.

13. The neural sensing device according to claim 9, wherein the control signal generator is connected to electrodes that are installed and connected to left side and right side of each of the sensing units of the array of sensing units, and the control signal generator transmits the control signal to the left side and the right side of each of the sensing units via the electrodes.

14. The neural sensing device according to claim 9, wherein the at control signal generator is connected to a ring electrode that is installed and connected to the periphery of each of the sensing units of the array of sensing units, and the control signal generator transmits the control signal to the ring electrode in the periphery of each of the sensing units via the ring electrode.

15. The neural sensing device according to claim 9, wherein the processed signal outputted by the signal processing module of the neural sensing device is used for stimulating at least one ganglion cell of a human retina.

16. The neural sensing device according to claim 9, wherein the processed signal is at least one electrical pulse.

* * * * *